United States Patent [19]

Sheehan et al.

[11] Patent Number: 5,390,675
[45] Date of Patent: Feb. 21, 1995

[54] TRANSCRANIAL DOPPLER PROBE MOUNTING ASSEMBLY WITH EXTERNAL COMPRESSION DEVICE/STRAP

[75] Inventors: Neil J. Sheehan, Palo Alto; Andras Boross, Belmont; Barry E. Zakar, Mountain View; Mary E. Rossman, Los Gatos, all of Calif.

[73] Assignee: Medasonics, Inc., Fremont, Calif.

[21] Appl. No.: 132,522

[22] Filed: Oct. 6, 1993

[51] Int. Cl.⁶ .................................................. A61B 8/00
[52] U.S. Cl. .......................... 128/661.07; 128/662.03; 128/662.04
[58] Field of Search ................... 128/660.01, 660.09, 128/661.05, 661.07, 662.03, 662.04, 24 AA; 606/130

[56] References Cited

U.S. PATENT DOCUMENTS

| | | | |
|---|---|---|---|
| 3,893,449 | 7/1975 | Lee et al. | 128/24 AA |
| 4,526,169 | 7/1985 | Narishige et al. | 606/130 |
| 4,817,621 | 4/1989 | Aaslid | 128/662.03 |
| 4,920,966 | 5/1990 | Hon et al. | 128/662.03 |
| 5,058,592 | 10/1991 | Whisler | 128/662.03 |
| 5,070,880 | 12/1991 | Gomez et al. | 128/662.03 |

Primary Examiner—George Manuel
Attorney, Agent, or Firm—Fliesler, Dubb, Meyer & Lovejoy

[57] ABSTRACT

A TCD probe mounting assembly is provided comprising a TCD probe mounted in a pedestal which has affixed to the base thereof an adhesive material for adhesively securing the pedestal to a patient's head. The pedestal is designed to allow insertion of the TCD probe therein after the pedestal is secured to a patient's head and for holding the probe at a selected angulation by means of friction after the probe is inserted in the pedestal. An external compression device and strap member are supplied to provide alternative means for providing a force perpendicular to a patient's head in order to minimize the risk of air gaps between the probe and the patient's head.

25 Claims, 7 Drawing Sheets

TRANSCRANIAL DOPPLER PROBE MOUNTING ASSEMBLY WITH EXTERNAL COMPRESSION DEVICE/STRAP

BACKGROUND OF THE INVENTION

1. Field of the Invention

The present invention relates to transcranial Doppler probe apparatus in general and in particular to an apparatus for mounting a transcranial Doppler probe to a patient's head.

2. Description of the Related Art

Since its introduction in 1982 by Aaslid et al., *Noninvasive transcranial doppler ultrasound recording of flow velocity in basal cerebral arteries*, J Neurosurgery 1982; 57:769–74, the transcranial Doppler (TCD) probe, an ultrasonic device for non-invasively and continuously measuring cerebral blood flow velocity, has been an invaluable research tool for investigators of neurophysiology.

In practice an investigator typically locates the Doppler signal by manipulating the probe over the appropriate cranial location. Once having found the signal the investigator fixes the probe in position, adjusts the angulation of the probe until a maximum amplitude signal is obtained and then locks the probe at the desired angulation.

Heretofore, most prior known and currently used TCD probe mounting assemblies employ relatively complex mechanisms, spring loaded thumbscrews, and the like for locking the probe in position after a maximum signal has been obtained. While effective for locking the probe in position, it has been found that all too often the manipulation of these locking devices disturb the delicate transducer positioning. As is well known, a translocation or angulation of the probe a fraction of a millimeter in any direction can result in loss or diminution of the signal.

SUMMARY OF THE INVENTION

In view of the foregoing, principal objects of the present invention are a method and apparatus comprising a TCD probe mounting assembly which includes a TCD probe, a pedestal, means for adjusting the angulation of the TCD probe in the pedestal and means for securing the pedestal to a patient's head.

The pedestal is designed to allow the insertion of the TCD probe therein after the pedestal is secured to a patient's head, as by an adhesive, and for holding the probe at a selected angulation by means of friction after the probe is inserted in the pedestal. A removable handle is fitted to the probe for setting the desired angulation of the probe. An external compression device or strap member are supplied to provide alternative means for providing a force perpendicular to a patient's head in order to hold the pedestal (and hence the probe) firmly against the patient's head thus minimizing the risk of air gaps between the probe and the head.

BRIEF DESCRIPTION OF THE DRAWINGS

The above and other objects, features and advantages of the present invention will become apparent from the following detailed description of the accompanying drawings, in which.

DESCRIPTION OF THE PREFERRED EMBODIMENTS

Figure 1:
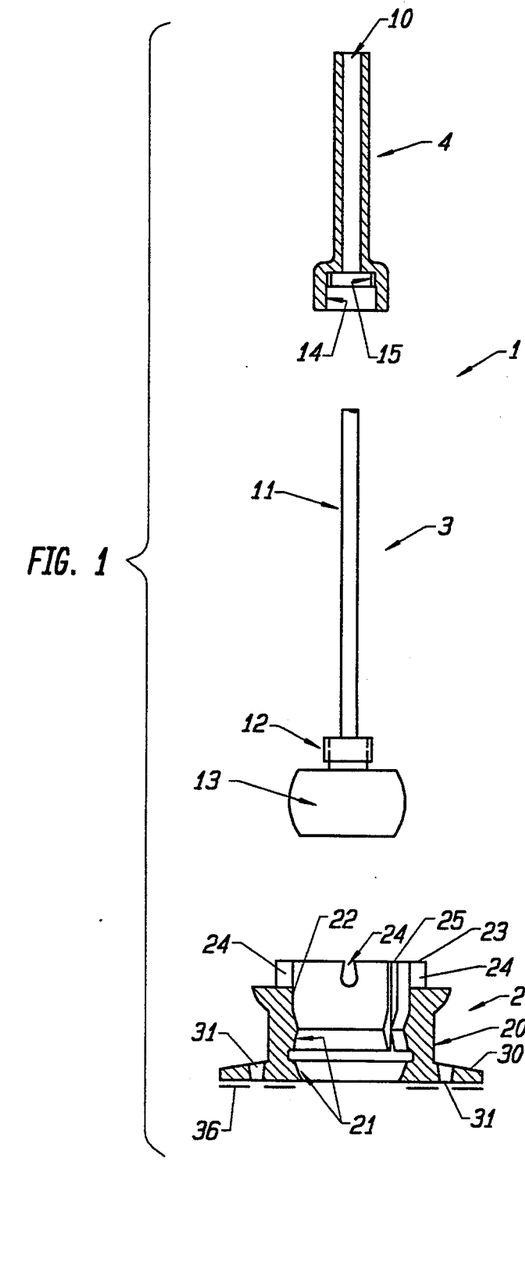
FIG. 1 is an exploded partial cross-sectional view of a TCD probe mounting assembly according to the present invention.
Figure 2:
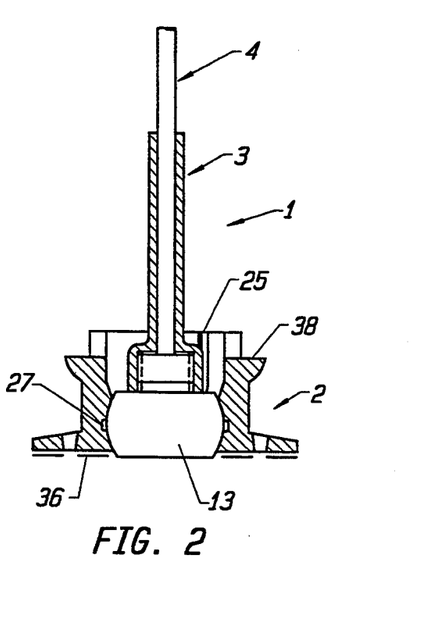
FIG. 2 is a partial cross-sectional view of the parts of FIG. 1 after they are assembled.

Referring to FIGS. 1 and 2, there is provided in accordance with the present invention a transcranial Doppler (TCD) probe mounting assembly designated generally as 1. In the assembly 1 there is a pedestal designated generally as 2, a TCD probe transducer assembly designated generally as 3 and a handle designated generally as 4.

Throughout the length of the handle 4 there is provided a through-hole 10 for a cable 11 which extends from a threaded stump 12 attached to the upper end of a spherically shaped TCD probe 13. At a lower end of the handle 4 there is provided a lead-in counter bore 14. At the bottom end of the lead-in counter bore 14 there is provided a single thread 15 for engaging the threaded stump 12 on the probe 3. It should be noted that the stump 12 could also be a smooth-walled stump which could be inserted in the lead-in bore 14 in a slip-fit manner. In practice, the handle 4 is provided to the user already on the transducer cable 11 when the TCD probe mounting assembly is manufactured and shipped to a customer.

The pedestal 2 comprises a hollow generally cylindrical member designated generally as 20. Member 20 is intended to be disposable and is made from an elastomeric material such as nitrile PVC, silicone rubber, or the like. Nitrile PVC is preferred because it provides less starting friction when the angulation of the probe 13 is adjusted, as will be described hereinbelow.

Located in the lower end of the interior wall of the member 20 there is provided a spherical retention cavity 21 that compressibly holds the transducer 13 with radial forces small enough to be overcome by the use of the handle 4 for steering purposes, as will be further described below, but large enough to prevent casual or accidental dislocation of the transducer. In other words, the transducer 13 will stay in position until intentionally moved. In general, the hardness of the material of the member 20 is approximately 70 Shore A durometer.

Above the spherical retention cavity 21 there is provided a spherical lead-in wall 22 which is provided to facilitate insertion of the transducer. Above the spherical lead-in wall 22 there is provided a protective wall 23. Wall 23 is provided for protecting the back end of the transducer 13 from being accidentally bumped. Extending through the wall 23 there is provided a plurality of four equally distant tear-drop slots 24, as shown more clearly in FIGS. 3-8. Slots 24 are used for housekeeping the transducer cable so as to prevent a tug on the cable from dislocating the transducer.

Figure 6:
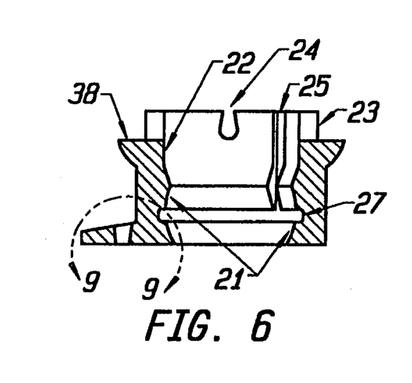
FIG. 6 is a cross-sectional view taken in the direction of lines 6—6 of FIG. 3.
Figure 7:
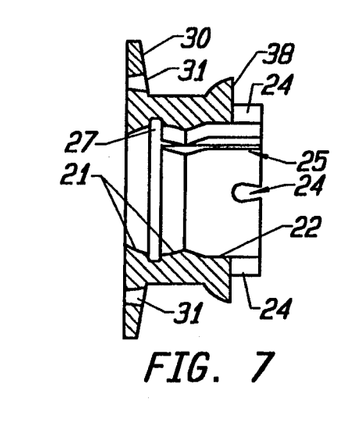
FIG. 7 is a cross-sectional view taken in the direction of lines 7—7 of FIG. 3.
Figure 8:
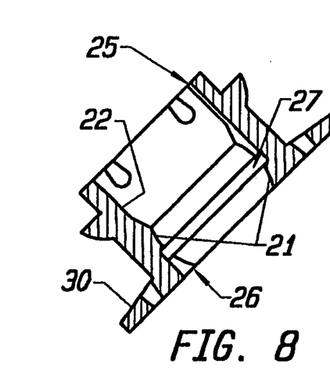
FIG. 8 is a cross-sectional view taken in the direction of lines 8—8 of FIG. 3.
Figure 9:
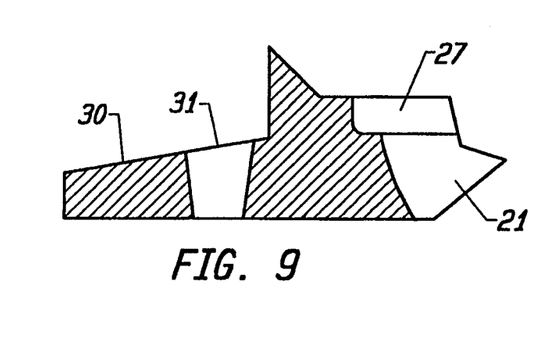
FIG. 9 is an enlarged detail view within the lines 9—9 of FIG. 6.

Referring to FIGS. 6-8, in the lead-in wall 22 and the spherical retention cavity 21 there is provided a pair of vertically extending slots 25 and 26, respectively. The slots 25 and 26 provide a path for air to escape from the pedestal when the probe 13 is inserted therein and also to provide an overflow path for excess ultrasound transmission gel. These slots are located 180 degrees from each other and intersect a central relief groove 27 which extends about the midline of the spherical retention cavity 21 in order to provide a maximum volume for excess gel and minimize the mechanical effect of the slots 25 and 26 on transducer retention.

Figure 25:
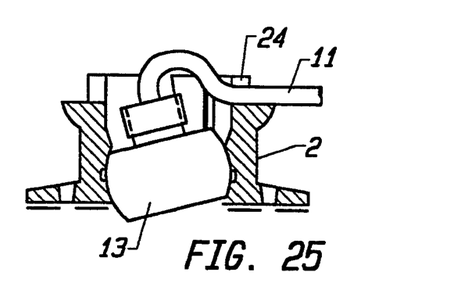

At its lower end the cylindrical member 20 comprises a pedestal flange 30. In the flange 30 there is-provided a plurality of holes 31, e.g., 3, that communicate with a corresponding number of slots 35 in a spacer 36, as shown most clearly in FIG. 10, which is adhesively attached to the bottom of the flange 30 as shown in FIGS. 1 and 2. The holes 31 provide a means for squirting additional ultrasound transmission gel under the face of the transducer 13 as required, as illustrated in FIG. 25.

Figure 3:
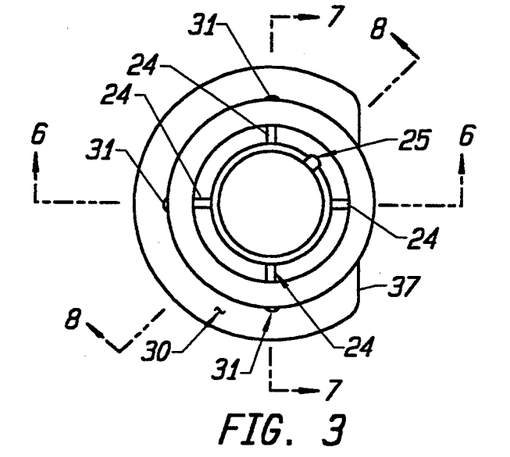
FIG. 3 is a top plan view of the pedestal of FIG. 1 according to the present invention.
Figure 4:
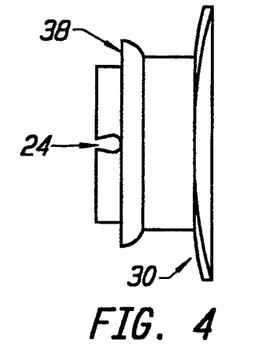
FIG. 4 is a side elevation view of FIG. 3.
Figure 5:
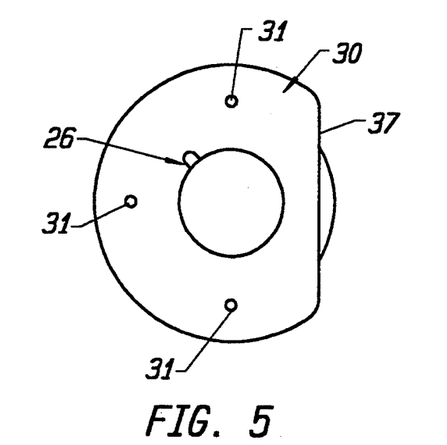
FIG. 5 is a bottom plan view of FIG. 3.

As seen most clearly in FIGS. 3 and 5, there is provided a flat surface 37 on one side of the pedestal flange 30 to facilitate pedestal positioning near a patient's ear. Extending radially from the wall 23 there is provided a ledge 38. As will be further described below with respect to FIGS. 11-20, the ledge 38 is used in conjunction with either an external compression device or an elastic strap to provide additional or an independent holding force on the pedestal member 20.

Figure 10:
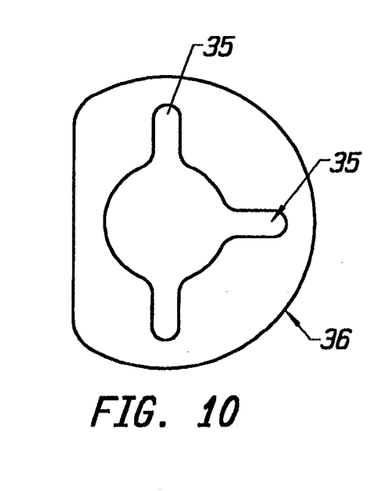
FIG. 10 is a plan view of an adhesive spacer according to the present invention.

Referring to FIG. 10, the spacer 36 comprises a sheet or patch of foam material, e.g. polyethylene, etc., with pressure sensitive adhesive (PSA) on both sides for allowing the pedestal 20 to better conform to head shape. The PSA on the pedestal side of the spacer 36 permanently bonds the spacer 36 to the pedestal 20. The slots 35 in the spacer 36, as previously indicated, communicate with the flange holes 31 in the pedestal 20 to allow ultrasound gel to flow therethrough. The spacer 36, which comes attached to the pedestal 20, is discarded after the procedure along with the pedestal 20. The spacer thickness is typically 1/32 of an inch.

Figure 11:
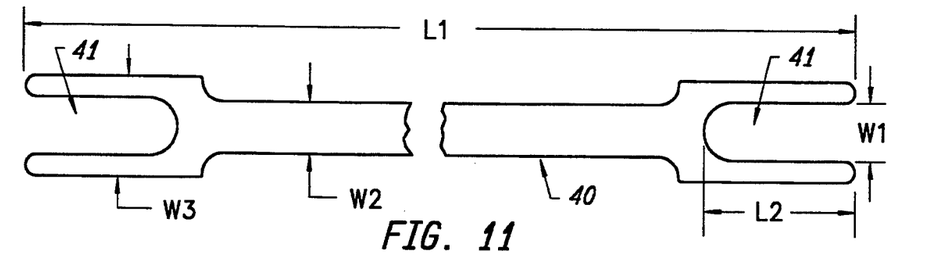
FIG. 11 is an unbent plan view of an external compression device according to the present invention.
Figure 12:
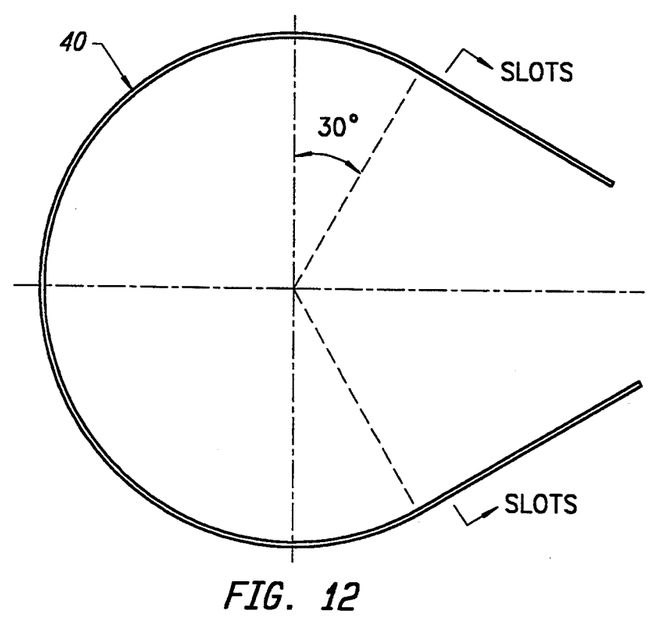
FIG. 12 is a side view of the device of FIG. 11 which is curved to fit over a patient's head.

Referring to FIGS. 11 and 12, the external compression device 40 is typically made of clear plastic, e.g. acrylic, etc., and in use provides a force perpendicular to a patient's head in order to hold the pedestal 20 and hence the transducer 13 firmly against the patient's head, thus minimizing the risks of air gaps between the transducer 13 and the patient's head and maintaining a good signal. At each end of the device 40 there is provided a slot 41. The slots 41, which are provided to rest on the pedestal ledge 38, are on both ends of the device 40 so as to permit bilateral sonography. A padded sheath (not shown) is provided for patient comfort to cover the non-working end of the device 40 in the case of unilateral monitoring.

In a typical embodiment, the device 40 has a length L1 of approximately 17 inches with a thickness of approximately 3/16 inch. The width W1 of each of the slots 41 is approximately 1.125 inches and the length L2 of the slots 41 is approximately 3.0 inches. The width W2 of the center section of the device 40 is approximately 0.75 inch. The outside width W3 of the fork members forming the slots 41 is approximately 2.0 inches. When formed, the member 40 describes a circular structure having a diameter of about 5 inches which extends about 120 degrees on both sides of a midline thereof. The slots 41 are located in that portion of the device 40 which is beyond or at the ends of the curved portion. The slots 41 allow the pedestal 20 to be positioned anywhere within the limits of the slot.

Referring to FIGS. 13-18, there is provided a strap member 45 made out of an elastomeric material, e.g. latex, etc. Strap member 45 is used as an alternative method of providing force like the device 40 of FIGS. 11 and 12. The strap member 45 has a plurality of female snap fasteners 46 at both ends in order to connect to male fasteners 47 on a pair of adhesively attachable anchor pads 48 which are attached to a patient's head and provide for variable tension and anchor pad location. The anchor pads 48 resemble traditional disposable ECG electrodes but contain no gel column center. Between the snap members 46 there is provided an elongated slot 49 in which the pedestal 20 is inserted, as will be described below.

Figure 13:
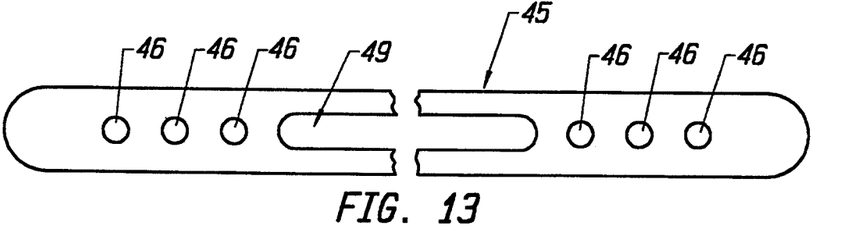
FIG. 13 is a foreshortened plan view of an elastic strap member according to the present invention.
Figure 14:
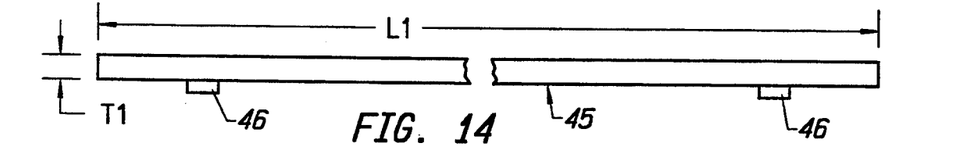
FIG. 14 is a side elevation view of FIG. 13.
Figure 15:
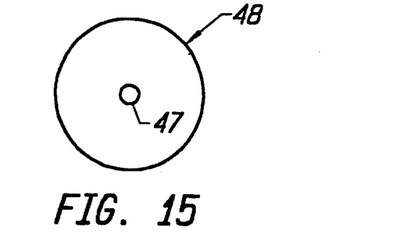
FIG. 15 is a top plan view of an adhesive pad with a snap member for use with the strap members of FIGS. 13 and 14 according to the present invention.
Figure 16:
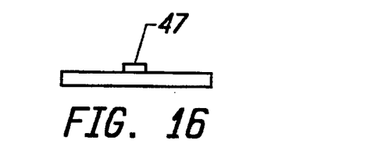
FIG. 16 is a side elevation view of FIG. 15.
Figure 17:
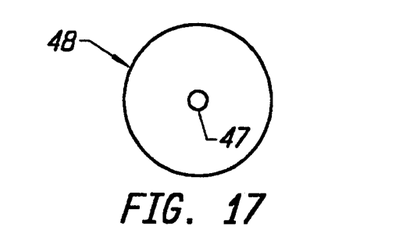
FIG. 17 is a plan view of a second adhesive pad member identical to the adhesive pad member of FIG. 15.
Figure 18:
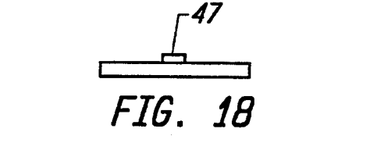
FIG. 18 is a side elevation of FIG. 17.

In a typical embodiment thereof, the length L1 of the strap member 45 is approximately 9 inches and the thickness T1 of the strap member 45 is approximately 1/16 inch.

In practice, the optimal transducer location is determined prior to attaching the pedestal 20 to a patient's head. This may be done with the subject transducer 13 with the handle 4 threaded onto the transducer stump 12 or with another handheld transducer. Ultrasound transmission gel is used in this process between the transducer and the patient's head.

Once found, the optimal location on the patient's head is or may be marked by any suitable means. Thereafter, the pedestal 20 is attached to the patient's head by centering the pedestal over the mark as viewed through the main opening in the pedestal using the pressure-sensitive adhesive on the patient side of the spacer 36 which was previously attached to the pedestal 20 during fabrication. The pedestal attachment area on the patient's head must be clean. The external compression device 40 described above with respect to FIGS. 11 and 12 or the strap member 45 as described above with respect to FIGS. 13-18 may be applied at this time, as shown in FIGS. 19 and 20, or after insertion of the transducer 13 in the pedestal 20.

Figure 19:
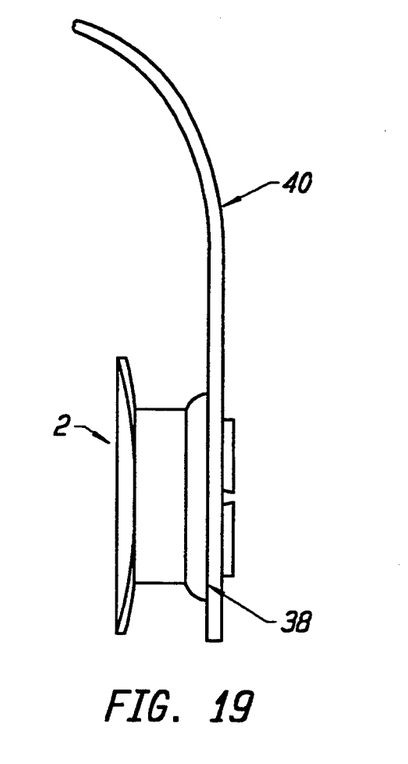
FIG. 19 is a partial side elevation view of the external compression device of FIGS. 11 and 12 with a TCD probe pedestal fitted therein according to the present invention.

Referring to FIG. 19, if the device 40 is used, the pedestal 20 is inserted in one of the slots 41 of the device 40 such that the device 40 rests on the ledge 38.

Figure 20:
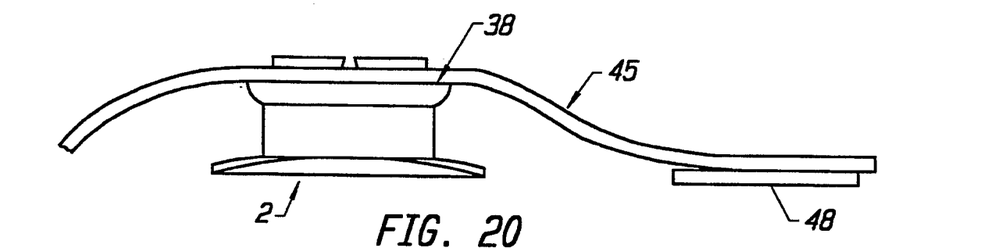
FIG. 20 is a partial side elevation view of the elastic strap member and adhesive pads of FIGS. 13–18 with a TCD probe pedestal fitted therein according to the present invention.

Referring to FIG. 20, if the strap member 45 is used, the same portion of the pedestal 20 is inserted through the slot 49 and one of the female snaps 46 on each end of the member 45 is snapped to an anchoring pad 48 which has been adhesively attached to a patient's head as shown in FIG. 20.

Figures 21, 22, 23:
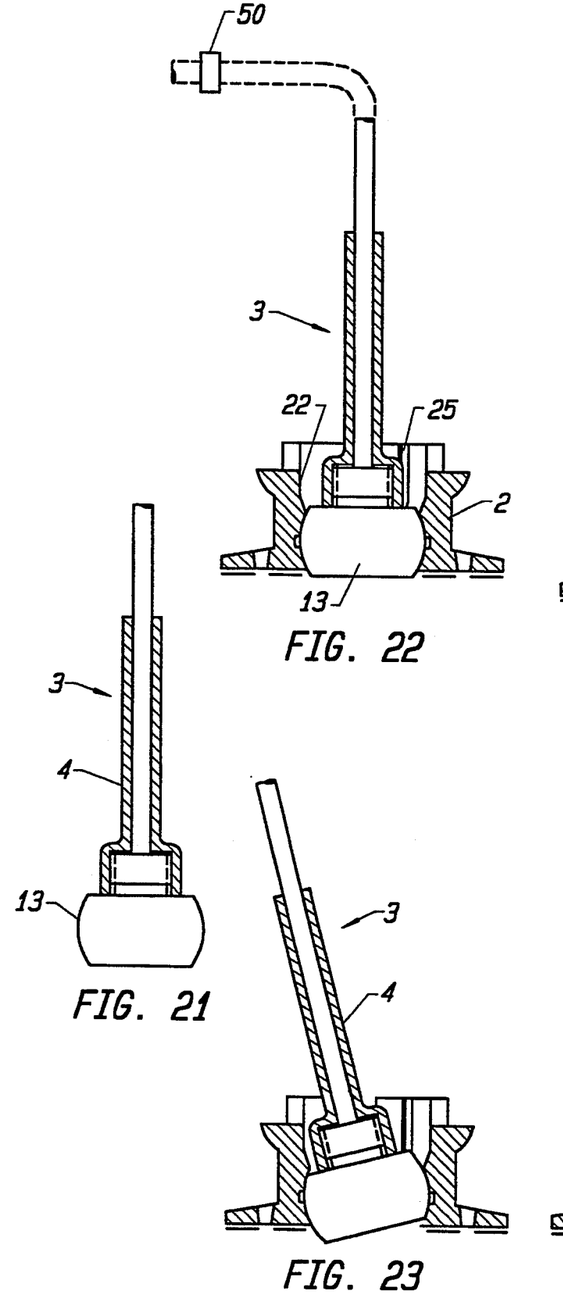
FIGS. 21–25 are cross-sectional views showing, respectively, each of five steps in the assembly and use of a TCD probe mounting assembly according to the present invention.

Referring to FIGS. 21–25 which illustrate the procedure for assembling and adjusting the TCD probe 13 and pedestal 20, if not already done, handle 4 is gently threaded onto transducer 13 with one simple turn. Lead-in is provided by the counter bore 14 in the handle front before the thread. After the handle 4 is threaded on the transducer 13 the transducer/handle assembly 3 is inserted into the pedestal 20 with a modest push. The transducer 13 is guided into the spherical retention cavity 21 by means of the spherical lead-in wall 22, as shown in FIG. 22. Ultrasound transmission gel may be placed on the working end of the transducer 13 prior to its insertion in the pedestal. Air that may be trapped inside pedestal 20 at the time the transducer 13 is inserted therein is allowed to bleed out by means of the upper and lower slots 25 and 26 in the spherical retention cavity 21 and lead-in wall 22, respectively, and the interconnecting central relief groove 27.

Figure 24:
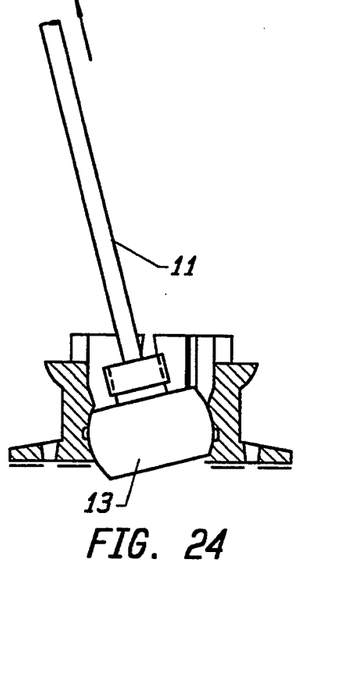

After the probe 13 is inserted in the pedestal 20, the probe 13 is spherically angled to the optimal position using the mechanical advantage provided by the length of the handle 4 as shown in FIG. 23. This provides for a very fine adjustment capability. After the desired angulation of the probe 13 is achieved, the handle 4 is gently unscrewed therefrom and slid down the cable 11 out of the way while the transducer 13 remains compressibly held in position by the spherical retention cavity 21, as shown in FIG. 24. For convenience, a handle stop member 50 which is fitted on the cable 11 as shown in FIG. 22 is provided to restrict the amount that the handle 4 is moved along the cable. In practice, the handle stop member 50 is located on the cable 11 approximately 12 to 18 inches from the transducer 13.

After the handle is removed from the probe 13, the cable 11 is pressed into the most convenient tear-drop slot 24 in the pedestal 20. At this point additional ultrasound transmission gel may be squirted under the transducer 13 through the most appropriate flange hole 31 via one of the slots 35 in the spacer 36 as shown in FIG. 25.

At the end of the procedure the external compression device 40 or strap 45 is first removed and then the pedestal/spacer/transducer assembly 3 is simply peeled off the side of the patient's head.

The advantage of the transcranial Doppler probe mounting assembly according to the present invention is that it is easily and instantly adjustable. There is no complex locking mechanisms that may disturb delicate transducer positioning. It is easy to assemble. It is disposable. There is no need to worry about careful cleaning of an intricate mounting system. All materials are non-metallic and therefore radio translucent. It is easy to place on a patient's head and easy to remove. There is no time-consuming application of collodion-type adhesive, colostomy cement, or dangerous solvent removal of same.

In a typical embodiment of the present invention, the flange 30 of the pedestal 20, with the exception of the flat side 37, has a radius of approximately 1 inch. The overall height of the pedestal 20 is approximately 0.875 inch. The height of the pedestal 20 from the bottom of the flange 30 to the top of the ledge 38 is approximately 0.688 inch. The diameter of the ledge 38 is approximately 1.5 inches and the outside of the wall 23 is approximately 1.125 inches. For a probe having a spherical diameter of approximately 0.875 inch, the radius of the spherical retention cavity 21 is approximately 0.431 inch and the diameter of the central relief groove 27 is approximately 0.938 inch.

As indicated above, the lower slot 26 communicates with the central relief groove 27 which in turn is in communication with the upper slot 25 such that both air and excessive ultrasound transmission gel which is squirted beneath the transducer 13 can escape from beneath the transducer 13 by passing through the slot 26, the central relief groove 27 and the slot 25.

While a preferred embodiment of the present invention is described above, it is contemplated that numerous modifications may be made thereto for particular applications without departing from the spirit and scope of the present invention. Accordingly, it is intended that the embodiments described be considered only as illustrative of the present invention and that the scope thereof should not be limited thereto but be determined by reference to the claims hereinafter provided.

What is claimed is:

1. A transcranial Doppler (TCD) probe mounting assembly comprising:
   a pedestal having a central bore, said central bore having a spherical retention cavity at its lower end for receiving and retaining a spherically-shaped TCD probe and a spherical lead-in wall above said spherical retention cavity for guiding a TCD probe into the spherical retention cavity when a TCD probe is inserted therein; and
   means for attaching the pedestal to a patient's head.

2. A TCD probe mounting assembly according to claim 1 wherein said attaching means comprises a flange member which extends radially outwardly from the bottom of said pedestal, said flange member having a plurality of holes for inserting ultrasound transmission gel beneath a TCD probe inserted in said pedestal.

3. A TCD probe mounting assembly according to claim 2 wherein said flange member comprises a flat side to facilitate pedestal positioning near an ear.

4. A TCD probe mounting assembly according to claim 1 wherein said pedestal comprises a flange on the lower end thereof and said attaching means comprises means for adhesively attaching said flange to a patient's head.

5. A TCD probe mounting assembly according to claim 4 wherein said adhesive attaching means comprises a sheet of adhesively coated foam material affixed to said flange.

6. A TCD probe mounting assembly according to claim 5 wherein said flange comprises a plurality of holes and said sheet of adhesively coated foam material comprises a corresponding number of slots for inserting ultrasound transmission gel beneath a TCD probe inserted in said pedestal.

7. A TCD probe mounting assembly according to claim 1 wherein said central bore comprises a passageway which extends from the bottom of said pedestal to the top of said pedestal to allow air to escape from beneath a TCD probe being inserted in said pedestal when said pedestal is affixed to a patient's head.

8. A TCD probe mounting assembly according to claim 7 wherein said passageway comprises:
   a first passageway which extends about the midline of said spherical retention cavity;
   a second passageway which extends vertically between the bottom of said pedestal and said first passageway; and
   a third passageway which extends vertically between the first passageway and the top of said pedestal.

9. A TCD probe mounting assembly according to claim 8 wherein said second passageway and said third passageway are angularly displaced relative to each other by a predetermined number of degrees.

10. A TCD probe mounting assembly according to claim 9 wherein said predetermined number of degrees is approximately 180 degrees.

11. A TCD probe mounting assembly according to claim 1 comprising a protective wall at the top of said pedestal for protecting the back end of a TCD probe inserted therein from being accidentally bumped.

12. A TCD probe mounting assembly according to claim 11 wherein said protective wall comprises a plurality of slots into which a cable extending from a TCD probe can be selectively inserted for preventing a tug on the cable from dislocating the TCD probe.

13. A TCD probe mounting assembly according to claim 1 comprising:
   a protective wall at the top of said pedestal for protecting the back end of a TCD probe inserted therein from being accidentally bumped; and wherein said attaching means comprises a ledge which extends radially outwardly from said wall upon which a holding force may be applied for holding the pedestal against a patient's head.

14. A TCD probe mounting assembly according to claim 13 comprising means for providing said holding force to said ledge for holding the pedestal against a patient's head.

15. A TCD probe mounting assembly according to claim 14 wherein said holding force providing means comprises an elongated, generally rectangular, curved member having a slot on at least one end thereof into which said pedestal may be inserted.

16. A TCD probe mounting assembly according to claim 15 wherein said curved member is curved to fit over a patient's head, said holding force comprises a spring force and said curved member comprises a material for providing said spring force.

17. A TCD probe mounting assembly according to claim 14 wherein said holding force providing means comprises:
   an elongated, generally rectangular, elastic member having a slot between the ends thereof into which said pedestal may be inserted; and
   means for attaching the ends of said elastic member to a patient's head.

18. A TCD probe mounting assembly according to claim 17 wherein said means for attaching the ends of said elastic member to a patient's head comprises means for adhesively attaching the ends of said elastic member to a patient's head.

19. A TCD probe mounting assembly according to claim 18 wherein said means for adhesively attaching the ends of said elastic member to a patient's head comprises a pair of adhesive pad members and said ends of said elastic member comprise means for attaching one of said ends to each of adhesive pad members.

20. A TCD probe mounting assembly according to claim 19 wherein said means for attaching one of said ends to each of adhesive pad members comprises snap fittings.

21. A TCD probe mounting assembly according to claim 1 comprising:
   means for adjusting the angulation of a TCD probe in said pedestal.

22. A TCD probe mounting assembly according to claim 21 wherein said adjusting means comprises;
   a handle member; and
   means for attaching said handle member to the TCD probe.

23. A TCD probe mounting assembly according to claim 22 wherein said TCD probe comprises a stump extending from the backside thereof and said means for attaching said handle member to the TCD probe comprises means for attaching said handle member to said stump.

24. A TCD probe mounting assembly according to claim 23 wherein said means for attaching said handle member to said stump comprises means for attaching said handle member to said stump in a friction tight manner.

25. A TCD probe mounting assembly according to claim 23 wherein said means for attaching said handle member to said stump comprises a thread on said stump and a mating thread in said handle member.

* * * * *